US011202669B2

(12) United States Patent
Norvell et al.

(10) Patent No.: US 11,202,669 B2
(45) Date of Patent: Dec. 21, 2021

(54) SURGICAL INSTRUMENTS WITH POSITION-DEPENDENT ACTUATOR COOPERATION AND IMPEDANCE

(71) Applicant: Ethicon LLC, Guaynabo, PR (US)

(72) Inventors: David K. Norvell, Monroe, OH (US); David J. Cagle, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 790 days.

(21) Appl. No.: 15/479,825

(22) Filed: Apr. 5, 2017

(65) Prior Publication Data

US 2018/0289415 A1    Oct. 11, 2018

(51) Int. Cl.
*A61B 18/14* (2006.01)
*A61B 17/00* (2006.01)
*A61B 18/00* (2006.01)

(52) U.S. Cl.
CPC .... *A61B 18/1445* (2013.01); *A61B 17/00234* (2013.01); *A61B 2017/00398* (2013.01);
(Continued)

(58) Field of Classification Search
CPC ............ A61B 18/1445; A61B 18/1442; A61B 2018/00642; A61B 2018/0091; A61B 2018/1455; A61B 17/00234
See application file for complete search history.

(56) References Cited

U.S. PATENT DOCUMENTS

| 7,189,233 | B2 * | 3/2007 | Truckai ............. | A61B 18/1442 606/49 |
| 9,044,243 | B2 * | 6/2015 | Johnson ................. | A61B 17/00 |

(Continued)

FOREIGN PATENT DOCUMENTS

| WO | WO-2014151621 A1 | 9/2014 |
| WO | WO-2014151952 A1 | 9/2014 |

OTHER PUBLICATIONS

International Search Report and Written Opinion for International App. No. PCT/US18/25869 dated Jul. 3, 2018 (8 pages).
(Continued)

*Primary Examiner* — Michael F Peffley
*Assistant Examiner* — Bo Ouyang
(74) *Attorney, Agent, or Firm* — Mintz Levin Cohn Ferris Glovsky and Popeo, P.C.

(57) ABSTRACT

Surgical instruments with position-dependent actuator cooperation and impedance are described herein. In general, movement of one actuator can cause proportional movement of another actuator depending upon the positions of each actuator. In one embodiment, a surgical instrument can include a distal end effector and a proximal actuator portion. First and second actuators coupled to the proximal actuator portion can each be configured to move between a first position and a second position. Further, the first actuator and the second actuator can be configured such that, when the first actuator and the second actuator are in the first position, moving the second actuator to the second position causes the first actuator to move to the second position, and when the first actuator is in the second position, the second actuator can be moved from the first position to the second position independent of the first actuator.

10 Claims, 14 Drawing Sheets

(52) U.S. Cl.
CPC ............ *A61B 2017/00734* (2013.01); *A61B 2018/0091* (2013.01); *A61B 2018/00642* (2013.01); *A61B 2018/1455* (2013.01)

(56) References Cited

U.S. PATENT DOCUMENTS

| | | | |
|---|---|---|---|
| 9,161,803 B2 | 10/2015 | Yates et al. | |
| 2007/0175958 A1 | 8/2007 | Shelton et al. | |
| 2009/0138003 A1* | 5/2009 | Deville | A61B 18/1445 606/33 |
| 2012/0078139 A1 | 3/2012 | Aldridge et al. | |
| 2014/0276738 A1 | 9/2014 | Price et al. | |
| 2015/0209059 A1 | 7/2015 | Trees et al. | |
| 2015/0209573 A1 | 7/2015 | Hibner et al. | |
| 2015/0282823 A1 | 10/2015 | Trees et al. | |
| 2017/0296212 A1* | 10/2017 | Ding | A61B 17/295 |
| 2018/0132925 A1* | 5/2018 | Allen, IV | A61B 18/1445 |

OTHER PUBLICATIONS

U.S. Appl. No. 15/200,283 entitled "Methods, Systems, and Devices for Initializing a Surgical Tool" filed Jul. 1, 2016.
U.S. Appl. No. 15/237,653 entitled "Methods, Systems, and Devices for Controlling a Motor of a Robotic Surgical Systems" filed Aug. 16, 2016.

* cited by examiner

SURGICAL INSTRUMENTS WITH POSITION-DEPENDENT ACTUATOR COOPERATION AND IMPEDANCE

FIELD

This disclosure relates generally to surgical instruments and, more particularly, to such instruments that include multiple actuators, such as triggers or other control mechanisms, that control various functions of an instrument.

BACKGROUND

A variety of surgical instruments are employed in various open, endoscopic, and laparoscopic surgeries. One group of such instruments can be utilized to manipulate tissue, seal tissue, and/or transect tissue. In some cases, these instruments can include a distal end effector having opposed jaw members that move relative to one another to grasp tissue therebetween. Certain of these instruments can also include a cutting mechanism that can be advanced through the grasped tissue to transect it. Electrical or other energy can also be delivered to the grasped tissue to seal the tissue prior to, or concurrent with, transection. For example, electrical energy can be applied to the grasped tissue by various mono-polar and bi-polar radio frequency (RF) electrodes or other energy delivery structures coupled to the jaw members. In other embodiments, ultrasonic energy can be applied to tissue by an oscillating element to effect tissue sealing and transection. In still other cases, mechanical fasteners, such as surgical staples, can be delivered to tissue in place of, or in addition to, electrical or other energy.

These surgical instruments can often include a proximal actuating portion from which the distal end effector is controlled. The proximal actuating portion can include a plurality of actuators, such as triggers or other control mechanisms, to control the various functions of the instrument. For example, a first trigger can control the opening or closing of the jaw members to grasp tissue, while a second trigger can control the operation of a cutting mechanism and/or the delivery of energy to seal tissue. The sequence with which a user actuates the plurality of triggers can be important in the optimal operation of the instrument because each of the plurality of triggers can control different functions of the instrument. For example, in use, a user can actuate a first trigger and hold or latch it in an actuated or closed position to securely grasp and compress tissue between the first and second jaw members, and then the user can actuate a second trigger to transect and/or seal the tissue.

Several different actuator configurations are known but can have associated disadvantages. For example, a plurality of triggers can be susceptible to user error whereby the user actuates the triggers in an incorrect sequence. For example, a user can inadvertently actuate a trigger configured to control transection and/or sealing of tissue before fully actuating and/or latching a trigger configured to control grasping tissue between the jaw members. Advancing a tissue transecting blade prior to securely grasping the tissue can result in poor blade performance, blade buckling, jaw damage, or other instrument failure. One reason for this is that sufficient tissue compression and immobilization can be important to both forming a good seal and facilitating passage of a cutting mechanism through the tissue.

Alternatively, a user can inadvertently release a trigger configured to control grasping tissue while another trigger configured to control transection and/or sealing of tissue is still actuated. Such an action can also result in incomplete tissue sealing and/or transection. Furthermore, actuation of a cutting element and/or energy-delivery elements in the above scenarios can pose injury risks to a patient by tissue unintentionally contacting a blade or activated energy delivery element.

Furthermore, such instruments can also pose a risk to users during handling and/or cleaning. For example, inadvertent actuation of a trigger configured to control tissue transection during handling and/or cleaning can result in exposure of the cutting element when the jaws are in an open position. The exposed cutting element can cause accidental injury to a user handling the instrument for cleaning, etc.

Still further, certain instruments having a plurality of actuators to control various functions do not provide an option for concurrent actuation of two or more functions using a single trigger. In certain embodiments, for example, concurrent actuation of a cutting element and movement of jaw members can require use of two actuators separately. In some cases, use of one actuator can be locked out until another actuator is locked in a fully actuated state. In some cases, however, a user may have a desire or need to operate a device in a non-standard manner, or may prefer to operate an instrument in a manner the user finds more efficient by controlling multiple actuators simultaneously. In many known instruments, such flexibility in operation is not possible.

Accordingly, there is a need for surgical instruments with improved actuators.

SUMMARY

The present disclosure generally provides surgical instruments and methods that include position-dependent actuator cooperation and impedance to permit flexibility in instrument operation while safeguarding against device damage or unintentional injury. The devices and methods described herein accomplish this in some embodiments by including cooperating features on a plurality of actuators that are configured to interact with one another depending upon the relative positions of the actuators. Examples can include a cam surface and a cam follower disposed on different actuators that can selectively contact one another to cause proportional movement of one actuator in response to movement of another actuator. By selectively linking actuator movements, users can be permitted to operate an instrument in a desired manner while complying with any required actuation order to prevent instrument damage or unintentional injury. Moreover, varying levels of impedance or required actuating force when actuators move independently versus when they are moved cooperatively can convey feedback to a user that the instrument is being actuated in a non-standard or perhaps non-optimal manner.

In one aspect, a surgical instrument is provided that can include an end effector configured to engage tissue, a first actuator operatively coupled to the end effector and configured to be actuated to cause the end effector to perform a first function, and a second actuator operatively coupled to the end effector and configured to be actuated to cause the end effector to perform a second function that is different than the first function. The first actuator and the second actuator can each be configured to move between a first position and a second position. Further, when the first actuator and the second actuator are in the first position, moving the second actuator to the second position is configured to cause the first actuator to move to the second position, and when the first actuator is in the second position, the second actuator is configured to move from the first position to the second position independent of the first actuator.

The instruments and methods described herein can have a number of additional features and/or variations, all of which are within the scope of the present disclosure. In at least some embodiments, for example, the end effector can further include a first jaw and a second jaw pivotally coupled to one another, as the surgical instrument can include a cutting element configured to translate along the end effector, the first actuator can be configured to be actuated to move the first jaw and the second jaw relative to one another between an open configuration and a closed configuration to grasp tissue therebetween, and the second actuator can be configured to be actuated to translate the cutting element along the end effector to cut the tissue grasped by the first jaw and the second jaw. In at least some embodiments, moving the first actuator from the first position to the second position can be configured to cause the first jaw and the second jaw to move to the closed position, and moving the second actuator from the first position to the second position can be configured to cause the cutting element to translate along the end effector. In at least some embodiments, the instrument can further include an electrode at the end effector configured to deliver radio frequency (RF) energy to the tissue grasped by the end effector.

In at least some embodiments, for another example, the first actuator can include a cam follower and the second actuator can include a cam surface, and the cam follower and the cam surface can be configured to move into and out of contact one another depending on relative positions of the first actuator and the second actuator. In at least some embodiments, the cam follower and the cam surface can be configured such that movement of the second actuator from the first position toward the second position causes proportional movement of the first actuator from the first position toward the second position. In at least some embodiments, the cam follower and the cam surface can be configured to prevent binding of the second actuator to the first actuator when the first actuator and the second actuator are in the second position.

In at least some embodiments, for yet another example, the first and second actuators can be configured to have different and/or variable impedances (e.g., as measured by a required actuation force) depending upon their positions. For example, a force required to move the second actuator to the second position when the first actuator and the second actuator are in the first position can be greater than a force required to move the second actuator to the second position when the first actuator is in the second position and the second actuator is in the first position. This greater amount of force required for actuation can serve as feedback to a user that the device is being operated in a non-standard or non-optimal manner. Despite the feedback, however, operation can be permitted with the application of greater actuation force because movement of one actuator can cause required movement of another actuator. As a result, in at least some embodiments, the second actuator can be moved from the first position to the second position regardless of a position of the first actuator. For example, the first actuator need not be latched or otherwise locked in a particular position, such as the second position, prior to the movement of the second actuator.

In at least some embodiments, for another example, the first actuator and the second actuator can be further configured such that, when the first actuator and the second actuator are in the second position, moving the first actuator to the first position can be configured to cause the second actuator to move to the first position, and when the second actuator is in the first position, the first actuator can be configured to move from the second position to the first position independent of the second actuator. Accordingly, various actuators can selectively cooperate and cause movement of one another during movements in both directions, e.g., actuation movements and release movements.

The first and second actuators described herein can have a variety of forms. In at least some embodiments, each of the first actuator and the second actuator can be a trigger pivotally coupled to a housing of the surgical instrument.

In another aspect, a surgical instrument is provided that can include an end effector having first and second jaws configured to grasp tissue, a cutting element configured to translate along the end effector to cut tissue grasped between the first and second jaws, a first actuator configured to control grasping of the tissue by the first and second jaws, a second actuator configured to control translation of the cutting element, a cam surface formed on one of the first actuator and the second actuator, and a cam follower formed on another of the first actuator and the second actuator. The first actuator and the second actuator can each be configured to move between a released position and an actuated position. The cam follower and the cam surface can be configured to contact one another such that movement of the second actuator from the released position to the actuated position is effective to move the first actuator proportionally toward the actuated position unless the first actuator is already in the actuated position.

A number of variations and additional features are possible. For example, in at least some embodiments the cam follower and the cam surface can be configured to be spaced apart from one another when the first actuator is in the actuated position such that the second actuator can move independently of the first actuator. For another example, in at least some embodiments, the cam follower and the cam surface can be configured to prevent binding of the second actuator to the first actuator when the first actuator and the second actuator are in the actuated position.

In at least some embodiments, for another example, the cam follower and the cam surface can be configured to contact one another such that movement of the first actuator from the actuated position to the released position is effective to move the second actuator proportionally toward the released position unless the second actuator is already in the released position.

In at least some embodiments, for yet another example, a force required to move the second actuator to the actuated position when the first actuator and the second actuator are in the released position can be greater than a force required to move the second actuator to the actuated position when the first actuator is in the actuated position and the second actuator is in the released position. In at least some embodiments, for another example, the second actuator can be moved from the released position to the actuated position regardless of a position of the first actuator. The increased actuation force can serve as feedback to a user that the instrument is being used in a non-standard or non-optimal manner, but such operation can be permitted with the application of greater actuation force and movement of one actuator can cause any required corresponding movement of another actuator.

In at least some embodiments, for still another example, the instrument can further include an electrode configured to deliver radio frequency (RF) energy to the tissue grasped by the end effector.

In at least some embodiments, for another example, the first and second actuators can have a variety of forms. In at least some embodiments, for example, each of the first actuator and the second actuator can be a trigger pivotally coupled to a housing of the proximal actuator portion.

In a further aspect, a surgical method is provided that can include moving a first actuator of a surgical instrument from a released position to an actuated position and thereby bring first and second jaws of an end effector of the surgical instrument closer to one another, and moving a second actuator of the surgical instrument from a released position to an actuated position and thereby translate a cutting element along the end effector and thereby cause proportional movement of the first actuator toward the actuated position when the first actuator is in the released position. The movement of the second actuator from the released position to the actuated position can be independent of the first actuator when the first actuator is in the actuated position.

A number of variations and additional steps are possible with the disclosed methods. For example, in at least some embodiments the method can further include moving the first actuator from the actuated position to the released position, and moving the first actuator from the actuated position to the released position can cause proportional movement of the second actuator toward the released position when the second actuator is in the actuated position, and the movement of the first actuator from the actuated position to the released position can be independent of the second actuator if the second actuator when in the released position. In at least some embodiments, for another example, the method can further include delivering radio frequency (RF) energy to tissue grasped between the first and second jaws of the end effector.

Any of the features or variations described above can be applied to any particular aspect or embodiment of the disclosure in a number of different combinations. The absence of explicit recitation of any particular combination is due solely to the avoidance of repetition in this summary.

DETAILED DESCRIPTION

Figure 1:
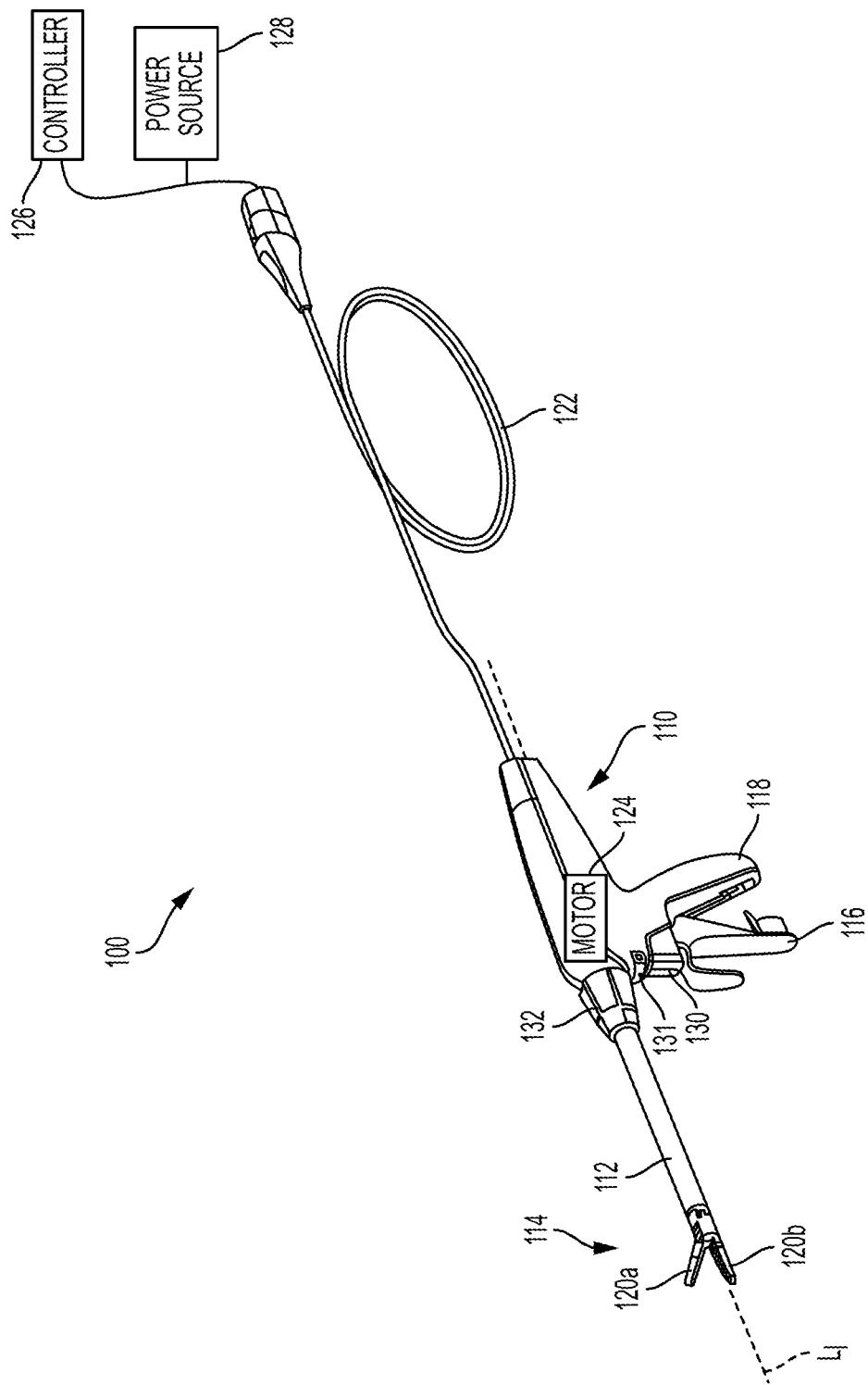
FIG. 1 is a perspective view of one embodiment of a surgical instrument according to the teachings of the present disclosure.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present application. To the extent features are described herein as being a "first feature" or a "second feature," such numerical ordering is generally arbitrary, and thus such numbering can be interchangeable. Further, in the present disclosure, like-numbered components of the various embodiments generally have similar features when those components are of a similar nature and/or serve a similar purpose.

Additionally, the figures are not necessarily to scale and, to the extent that linear or circular dimensions are used in the description of the disclosed devices and methods, such dimensions are not intended to limit the types of shapes that can be used in conjunction with such devices and methods. A person skilled in the art will recognize that an equivalent to such linear and circular dimensions can be determined for any geometric shape. Still further, sizes and shapes of the devices, and the components thereof, can depend at least on the anatomy of the subject in which the devices will be used, the size and shape of components with which the instruments will be used, and the methods and procedures in which the devices will be used.

Surgical instruments and methods of using such instruments are described herein, where two or more actuators of the surgical instruments are configured to cooperate with one another (e.g., operation of one actuator may cause or prevent operation of another actuator) in a position-dependent manner. Such position-dependent cooperation of two or more actuators may serve as a safety feature to prevent out-of-sequence misuse of surgical instruments having two or more actuators. For example, in a surgical instrument that includes first and second actuators (e.g., for grasping and transecting tissue, respectively), inadvertent actuation of the second actuator before actuation of the first actuator can cause substantially simultaneous actuation of both first and second actuators (i.e., cooperation of the first and second actuators) while providing increased impedance or resistance feedback to a user. Moreover, when both the first and second actuators are actuated, the first actuator can be prevented from returning to a released position until the second actuator is similarly released. Such selective trigger cooperation can be accomplished, for example, by coupling a cam and a cam follower to opposite ones of the first and second actuators such that the cam and the cam follower interact with each other when the actuators are in certain positions.

FIG. 1 illustrates one embodiment of a surgical instrument 100 according to the teachings provided herein. The instrument 100 can be configured to grasp and transect, or cut, tissue, though a variety of other functions are possible in other embodiments of the instrument. The surgical instrument 100 can include a proximal actuator portion 110, a shaft 112 extending distally therefrom, and a distal end effector 114 configured to interact with tissue at a surgical site.

The proximal actuator portion 110 can have a variety of shapes and sizes. For example, the proximal actuator portion 110 can be any type of pistol-grip or other type of handle known in the art that can be configured to carry various actuators, such as levers, triggers, buttons, or sliders that can control functionality of the end effector 114. In the illustrated embodiment, the proximal actuator portion 110 includes a first actuator 116 and a second actuator 130 that are both in the form of a trigger that can pivot relative to a stationary grip 118. Movement of any of the first actuator 116 and the second actuator 130 toward and away from the stationary grip 118, such as by manual movement by a hand of a user, can cause performance of an end effector function. In the illustrated embodiment, for example, moving the first actuator 116 from the position shown in FIG. 1 to a position immediately adjacent to the grip 118 can cause first and second jaws 120a, 120b of the end effector 114 to move from the open configuration shown in FIG. 1 to a closed configuration in which the jaws 120a, 120b are approximated or immediately adjacent to one another. Similar movement of the second actuator 130 can be configured to distally extend a blade along a length of the end effector 114 to transect tissue grasped by the first and second jaws 120a, 120b. The illustrated embodiment further includes a third actuator 131 and a fourth actuator 132. The third actuator 131 can be configured to deliver radio-frequency (RF) electrical energy to tissue grasped by the first and second jaws 120a, 120b via one or more electrodes or other energy delivery structures coupled thereto. The fourth actuator 132 can be configured to control rotation of the end effector 114 about a longitudinal axis $L_I$ of the instrument 100.

In some embodiments, the proximal actuator portion 110 can be configured for use with a robotic surgery platform, as opposed to a user's hand. In such embodiments, the first, second, third, and fourth actuators 116, 130, 131, 132 can have different configurations than shown in the embodiment of FIG. 1, such as by being included as part of a tool housing configured to be operatively coupled to the robotic surgery platform to allow the robotic surgery platform to provide inputs to the tool housing to selectively actuate the first, second, third, and fourth actuators 116, 130, 131, 132. Various embodiments of tool housings of surgical instruments configured to be operatively coupled to a robotic surgery platform are further described in International Pat. Pub. No. WO 2014/151952, entitled "Compact Robotic Wrist," filed Mar. 13, 2014; International Pat. Pub. No. WO 2014/151621, entitled "Hyperdexterous Surgical System," filed Mar. 13, 2014; U.S. patent application Ser. No. 15/200,283, entitled "Methods, Systems, And Devices For Initializing A Surgical Tool," filed Jul. 1, 2016; and in U.S. patent application Ser. No. 15/237,653 entitled "Methods, Systems, And Devices For Controlling A Motor Of A Robotic Surgical System" filed Aug. 16, 2016; the entire contents of which are hereby incorporated by reference.

Referring again to FIG. 1, the shaft 112 can extend distally from the proximal actuator portion 110 and can have a bore or lumen (not shown) extending therethrough. The bore can carry mechanisms for transmitting movement of the first actuator 116 (and any other actuators, as described below) to the end effector 114, such as any of drive shafts, cables, rods, etc. In some embodiments, the instrument 100 can be configured for purely mechanical user-powered operation via various linkages, gear sets, etc. In other embodiments, the instrument 100 can include one or more motors 124 (e.g., an electric motor, etc.) coupled to a power source 128 (e.g., a battery, etc.) and one or more controllers 126 (e.g., a digital data processor, etc.) that can provide power for operating the device in response to sensed actuation of one or more actuators or other control mechanisms. Such components can be included in the proximal actuator portion 110, as shown by the motor 124 in FIG. 1, or can be disposed external to the proximal actuator portion 110, as shown by the power source 128 and the controller 126, and connected thereto via one or more cables, such as a cable 122.

The end effector 114 can have a variety of sizes, shapes, and configurations. As shown in more detail in FIG. 2, the end effector 114 can include a first, upper jaw 120a and a second, lower jaw 120b each disposed at a distal end 112d of the shaft 112. The first and second jaws 120a, 120b can extend along a longitudinal axis $L_I$ of the instrument 100 and can be configured to pivot relative to one another about a pivot axis $A_P$. Both of the jaws 120a, 120b can be moveable relative to the shaft 112 such that the end effector 114 can be moved between open and closed configurations, or only one of the upper and lower jaws 120a, 120b can be configured to move relative to the shaft 112 and to the other of the jaws 120a, 120b to move the end effector 114 between open and closed configurations. In the illustrated embodiment, the upper jaw 120a is configured to pivot relative to the shaft 112 and relative to the lower jaw 120b while the lower jaw 120b remains stationary. When the end effector 114 is in the open configuration illustrated in FIG. 2, the jaws 120a, 120b can be positioned a distance apart from one another with space between. When the end effector 114 is in a closed configuration, a longitudinal axis of the upper jaw 120a can be substantially parallel to a longitudinal axis of the lower jaw 120b (with the longitudinal axes of each jaw being substantially parallel to the longitudinal axis $L_I$ of the instrument 100) and the jaws 120a, 120b can be moved toward one another such that a distance therebetween is less than when the end effector 114 is in the open configuration.

The first and second jaws 120a, 120b can have a substantially elongate and straight shape in some embodiments, while in other embodiments one or both of the jaws 120a, 120b can be curved along a length thereof. Moreover, a longitudinal axis of the end effector 114 can be parallel to and coaxial with the longitudinal axis $L_I$ of the instrument 100 at least when the end effector 114 is in the closed configuration and, if the end effector 114 is configured to articulate relative to the shaft 112, when the end effector 114 is not articulated relative to the shaft 112. The jaws 120a, 120b can have any suitable axial length $L_A$ for engaging tissue. The axial length $L_A$ of the jaws 220a, 220b can also be selected based on the targeted anatomical structure for transection and/or sealing. In one embodiment, the jaws 120a, 120b can have a substantially equal axial length $L_A$, though use of different length jaws is possible in other embodiments.

The first and second jaws 120a, 120b can have any number and any combination of features configured to facilitate grasping tissue therebetween. For example, tissue engagement surfaces 222a, 222b of the first and second jaws 120a, 120b, respectively, can be configured to directly contact tissue in some embodiments. In other embodiments, either one or both of the engagement surfaces 222a, 222b can include one or more surface features formed thereon that can help secure tissue. The one or more surface features can facilitate grasping of tissue, can be configured to increase friction between the tissue and the engagement surfaces 222a, 222b of the jaws 120a, 120b without tearing or otherwise damaging the tissue in contact with such surface features, and/or can facilitate forming substantially smooth, uniform layers of tissue. Examples of the surface features can include teeth, ridges, and depressions.

Moreover, in some embodiments the tissue engagement surfaces 222a, 222b can include one or more electrodes or other energy delivery structures coupled thereto. In the illustrated embodiment, tissue engagement surface 222b includes an electrode 221 disposed thereon. The electrode 221 can be coupled via a conductor (not shown) to the controller 126, power source 128, and third actuator 131 to selectively deliver electrical energy, such as radio-frequency (RF) electrical energy, to tissue in contact therewith. In other embodiments, the third actuator 131 can be omitted and, for example, the second actuator 130 can be configured to selectively deliver tissue sealing energy and transect tissue. Examples of applying energy are described further in U.S. Pat. Pub. No. 2012/0078139, entitled "Surgical Generator for Ultrasonic and Electrosurgical Devices," filed Oct. 3, 2011; U.S. Pat. No. 9,161,803, entitled "Motor Driven Electrosurgical Device With Mechanical And Electrical Feedback," filed Jun. 2, 2011; and U.S. Pat. Pub. No. 2015/0209573, entitled "Surgical Devices Having Controlled Tissue Cutting And Sealing," filed Jan. 28, 2014; the entire contents of which are hereby incorporated by reference.

As discussed, for example, in previously mentioned U.S. Pat. Pub. No. 2012/0078139, entitled "Surgical Generator for Ultrasonic and Electrosurgical Devices," filed Oct. 3, 2011, RF energy is a form of electrical energy that may be in the frequency range of 300 kHz to 1 MHz. The instrument 100 can be configured to transmit low frequency RF energy through tissue, which causes ionic agitation, or friction, in effect resistive heating, thereby increasing the temperature of the tissue. Because a sharp boundary can be created between treated tissue and surrounding tissue, users of the instrument 100, e.g., surgeons and/or other medical professionals, can operate on the tissue with a high level of precision and control without sacrificing un-targeted adjacent tissue. The low operating temperatures of RF energy can be useful for removing, shrinking, or sculpting soft tissue while simultaneously sealing blood vessels. RF energy can work particularly well on connective tissue, which is primarily comprised of collagen and which shrinks when contacted by heat. Heat generated by current flow from the RF energy through tissue to which the RF energy is applied can seal the tissue, e.g., form hemostatic seals within the tissue and/or between tissues, and can thus be particularly useful for sealing blood vessels, for example. When the instrument 100 includes a blade or other cutting element configured to cut tissue clamped between the jaws 120a, 120b, as described below, and is configured to apply energy to tissue clamped between the jaws 120a, 120b to seal the tissue, the instrument 100 can be configured to separately cut and seal tissue clamped between the jaws 120a, 120b or can be configured to simultaneously cut and seal tissue clamped between the jaws 120a, 120b.

Figure 2:
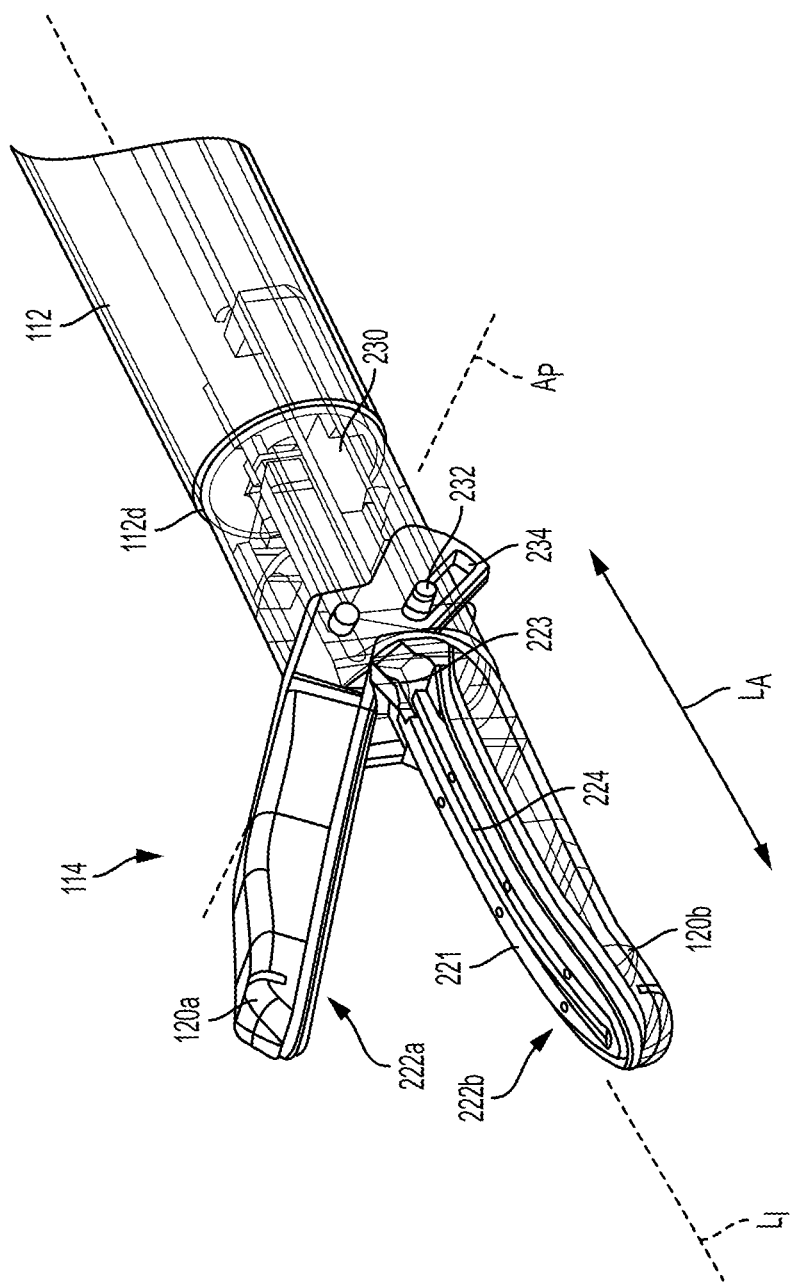
FIG. 2 is a partially transparent perspective view of a distal portion of the instrument of FIG. 1.

Tissue transection can be accomplished using a cutting element, such as the blade 223 shown in FIG. 2, configured to transect tissue captured between the jaws 120a, 120b. The cutting element can have various sizes, shapes, and configurations. Examples of a cutting element include a knife blade and a sharp edge. The cutting element can be sized and shaped to cut various thicknesses and types of tissue positioned between the jaws 120a, 120b of the end effector 114, and can have a sharp or serrated distal edge configured to transect tissue. In the illustrated embodiment, the second actuator 130 can be configured to control proximal and distal translation of the blade 223 along at least a portion of the length $L_A$ of the jaws 120a, 120b to transect tissue grasped therebetween. The blade 223 can be configured to ride within a slot 224 extending along a length of each jaw 120a, 120b (the slot in the first jaw 120a is obscured in FIG. 2).

As noted above, the surgical instrument 100 can include a first actuator or trigger 116 configured to open and close the jaws 120a, 120b of the end effector 114 and a second actuator or trigger 130 configured to advance the cutting element 223. Manipulation of the first, closure actuator 116 (e.g., by manual manipulation by a user) can cause the end effector 114 to move between the open and closed configurations described above. In other words, manipulation of the first actuator 116 can cause one or both of the jaws 120a, 120b to pivot or otherwise move to allow the jaws 120a, 120b to engage tissue, move anatomical structures, and/or perform other surgical functions. The first actuator 116 can have various sizes, shapes, and configurations. As in the illustrated embodiment, the first actuator 116 can be moveable toward and away from the stationary grip 118, such as via pivoting. The first actuator 116 can have a first, released position in which the actuator is pivoted away from the stationary grip 118 and in which the jaws 120a, 120b are open. The first actuator 116 can also have a second, actuated position that is different from the first position and in which the actuator is positioned adjacent to, or substantially in contact with, the stationary grip 118 and in which the jaws 120a, 120b can engage tissue and apply a force to tissue disposed therebetween. The first actuator 116 can be biased to the first, released position in some embodiments.

The first actuator 116 can be configured to move the jaws 120a, 120b between the open and closed configurations using manual or powered components. In one manually actuated embodiment, the first actuator 116 can be coupled to a translating shaft 230 via a linkage 650 (see FIG. 6) and pivoting movement of the first actuator 116 toward the stationary grip 118 can translate the shaft 230 proximally. This proximal translation can be transferred to a pin 232 that can be disposed within a slot 234 formed in the first jaw 120a. Translation of the pin 232 within the slot 234 can cause the first jaw 120a to pivot towards the second jaw 120b, thereby capturing tissue therebetween. Mechanical linkages other the illustrated linkage 650 are possible, including, e.g., a gear and rack, etc. In a powered embodiment, for example, an instrument can make use of one or more motors (e.g., the motor 124 disposed within the proximal actuator portion 110 or a motor disposed outside of the proximal actuator portion and being attachable thereto via wired connection similar to the cord 122) to effect opening and closing of the end effector jaws 120a, 120b. The motor 124 can include any type of motor (e.g., a rotary motor, etc.) configured for use with a surgical instrument. The motor, such as the motor 124, can be coupled to the controller 126 and the power source 128. The controller 126 can include a variety of devices configured to process signals (e.g., a microprocessor, a central processing unit (CPU), a memory controller, etc.), and the power source 128 can include any of a variety of devices configured to supply power to at least the controller 126 (e.g., a battery, etc.). In some embodiments, the motor 124, the controller 126, and/or the power source 128 can be off-board instead of on-board the instrument 100, such as by the instrument 100 being attachable via wired connection similar to the cord 122 to, e.g., an electrical outlet or other off board power source and/or a generator. In such embodiments, a manual movement of the first actuator 116 can be configured to cause the controller 126 to transmit a control signal to the motor 124, which can cause the jaws 120a, 120b to open or close. Further, the first actuator 116 can interact with one or more locking features 660 (see FIG. 6), e.g., a latch, etc., configured to lock the first actuator 116 relative to the stationary grip 118. For example, the one or more locking features 660 can automatically engage when the first actuator 116 substantially contacts the stationary grip 118.

The first and second actuators or triggers 116, 130 can cooperate to allow selective firing and closing of the instrument 100. The second actuator 130 can be configured to be actuated to advance the cutting element 223 through the end effector 114 and in some embodiments to apply energy to tissue. Depressing or pivoting the second actuator 130 can activate various elements in the instrument 100, thereby causing one or more actions such as the cutting element 223 advancing distally or retracting proximally relative to the jaws 120a, 120b, and/or energy being delivered to tissue disposed between the jaws 120a, 120b via one or more electrodes 221. As with the first actuator 116 described above, this can be accomplished manually or via powered motor drive. In a motor-powered embodiment, the second actuator 130 can be in electrical communication with the motor 124 (or off board motor) and the motor 124 (or off board motor) can be operatively coupled to the cutting element 223 using, e.g., a gear and rack. In such an embodiment, activation of the motor 124 (or off board motor) can cause advancement and/or retraction of the cutting element 223.

In a motor-powered embodiment, the instrument 100 can include at least one sensor (not shown) and the motor 124 can be configured to provide an output that is based at least in part on an output from the sensor. The controller 126 can be configured to determine an amount of power to be provided by the motor 124. The controller 126 can be configured to receive an output signal from the sensor and, based on the output signal from the sensor, cause the motor 124 to provide an output that supplies power to the cutting element 223. Various embodiments of motor control based on sensor output are further described in U.S. Pat. Pub. No. 2015/0282823, entitled "Methods And Devices For Controlling Motorized Surgical Devices," filed Apr. 8, 2014; and U.S. Pat. Pub. No. 2015/0209059, entitled "Methods And Devices For Controlling Motorized Surgical Devices," filed Jan. 28, 2014; the entire contents of which are hereby incorporated by reference.

Figure 3:
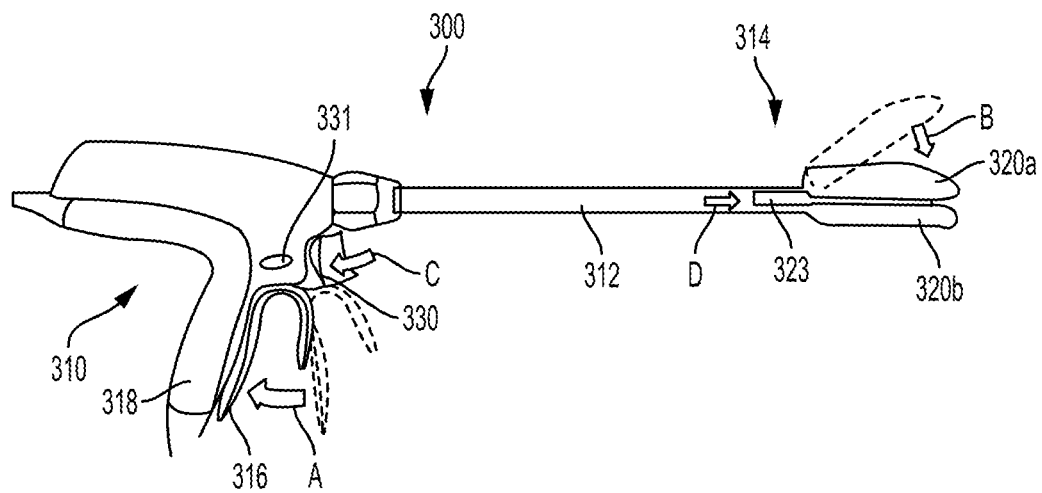
FIG. 3 is a side view of one embodiment of a surgical instrument showing operation of multiple actuators to control multiple instrument functions.
Figure 4:
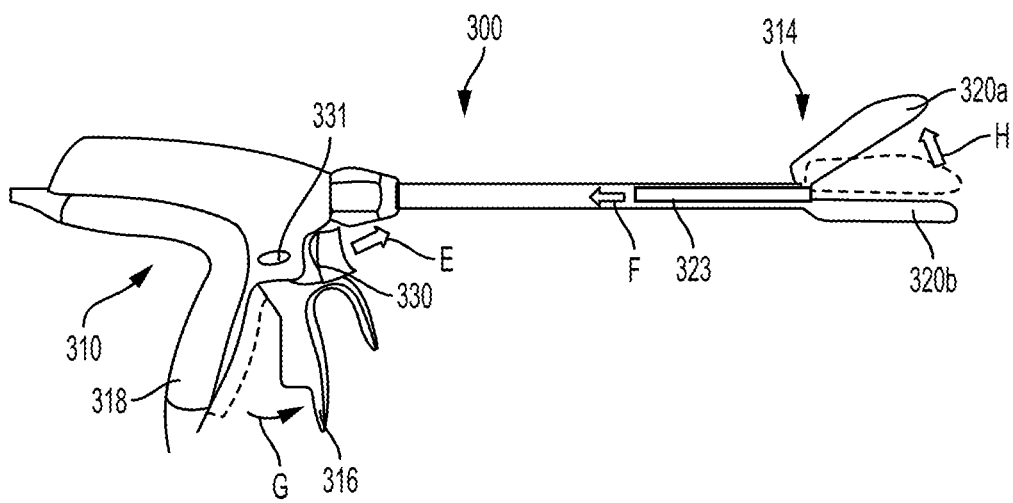
FIG. 4 is a side view of the surgical instrument of FIG. 3 showing further operation of multiple actuators to control multiple instrument functions.

FIGS. 3 and 4 illustrate one embodiment of a use sequence for another embodiment of a surgical instrument 300 configured to grasp and transect tissue using an end effector 314. A surgeon or other user can begin by positioning the jaws 320a, 320b of the end effector 314 such that tissue to be transected is disposed therebetween. The user would then actuate the first actuator 316 by pivoting it toward the stationary grip 318, as shown by arrow A in FIG. 3. This movement of the first actuator 316 can cause the first jaw 320a to pivot toward the second jaw 320b, as shown by arrow B, thereby grasping tissue between the jaws 320a, 320b. The user can then actuate the second actuator 330 by pivoting or depressing the actuator 330, as shown by arrow C. Movement of the second actuator 330 can cause distal advancement of the cutting element 323, as shown by arrow D. As noted above, tissue sealing electrical energy can also be activated by the second actuator 330 or by a separate actuator, such as the button 331.

After tissue transection and/or sealing is complete, a user can release the tissue by following the sequence shown in FIG. 4. More particularly, the user can release the second actuator 330, as shown by the arrow E, which can proximally retract the cutting element 323, as shown by the arrow F. Finally, the user can release the first actuator 316, as shown by the arrow G, which can cause the first jaw 320a to pivot away from the second jaw 320b, as shown by the arrow H, thereby releasing the transected and/or sealed tissue.

The use sequence of FIGS. 3 and 4 can be susceptible to user error in certain situations. For example, a user may actuate the various actuators in a different sequence than is described above. For example, a user may inadvertently actuate the second trigger 330 without prior or substantially simultaneous actuation of the first trigger 316. Such an action can cause the cutting element 323 to extend distally while the jaws 320a, 320b are in an open configuration, which can result in incomplete transection, blade buckling, jaw damage, and/or unintentional injury to a user and/or a patient subject. In another example, a user may inadvertently release the first trigger 316 before releasing the second trigger 330. Such an action can cause opening of the jaws 320a, 320b (e.g., releasing the grasped tissue) while the cutting element 323 is still in an extended position, thereby cutting short the transection and/or sealing process and exposing a sharp edge of the cutting element 323, which can cause unintended injury to a user and/or patient. These types of inadvertent actuations can occur both during a surgical procedure and during non-surgical handling of the instrument, such as during cleaning by a user, etc.

FIGS. 5-12A illustrate various features of the surgical instrument 100 that may prevent the above-described undesirable operating modes of a surgical instrument configured to grasp and transect tissue. In particular, the instrument 100 includes actuators having features that selectively cooperate with one another dependent on their respective positions to ensure proper operation of the device. Moreover, the position-dependent cooperation of the various actuators can also provide varying levels of actuator impedance (e.g., required actuating force) to provide feedback to a user of non-standard or non-optimal operation while permitting such operation if desired and ensuring safety regardless of operation order.

Figure 5:
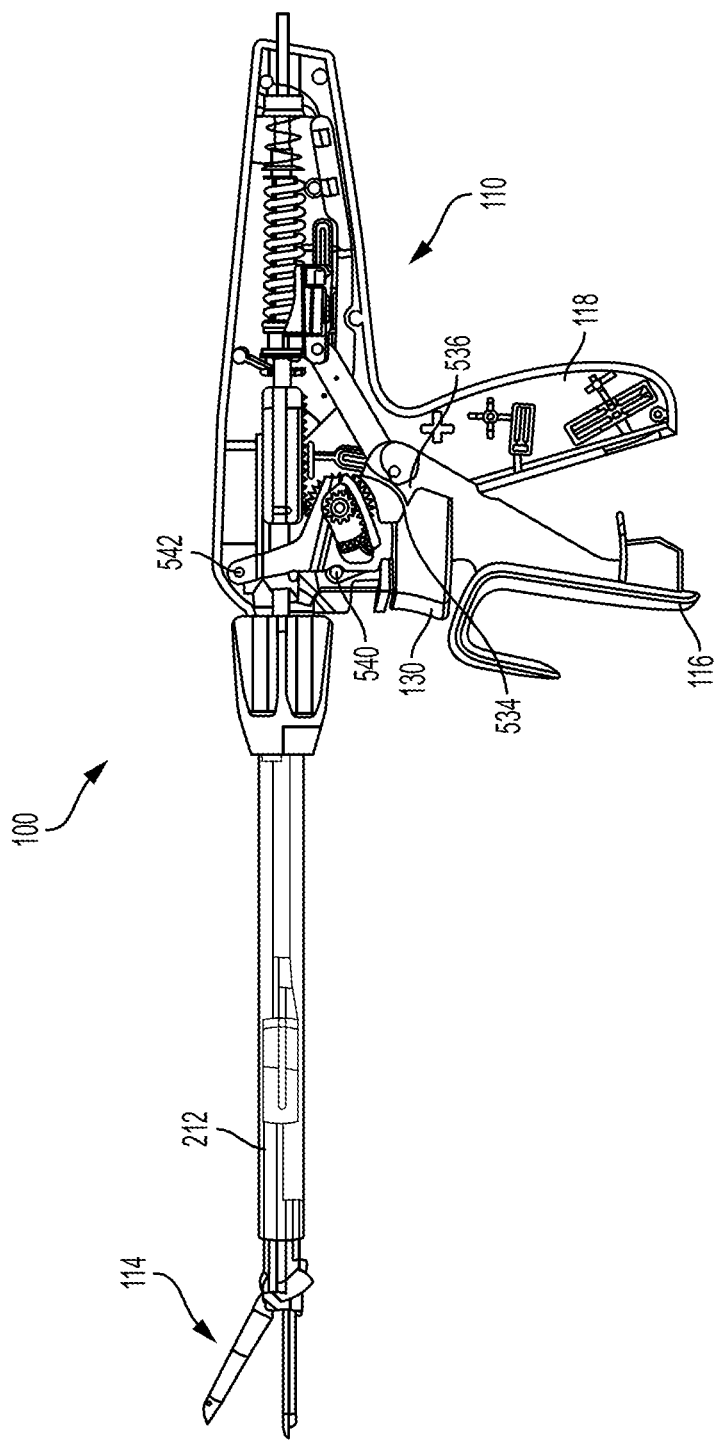
FIG. 5 is a partial cutaway side view of the surgical instrument of FIG. 1.
Figure 6:
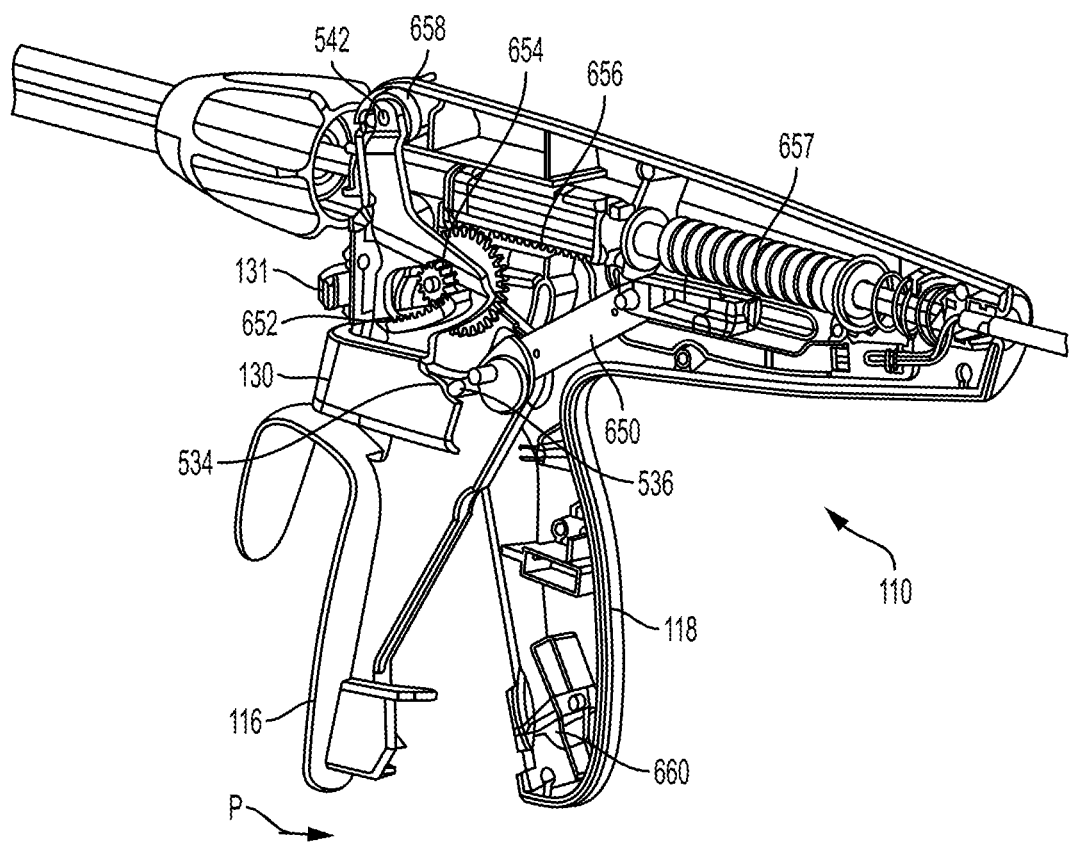
FIG. 6 is a partial cutaway perspective view of a proximal portion of the surgical instrument of FIG. 1.
Figure 7A:
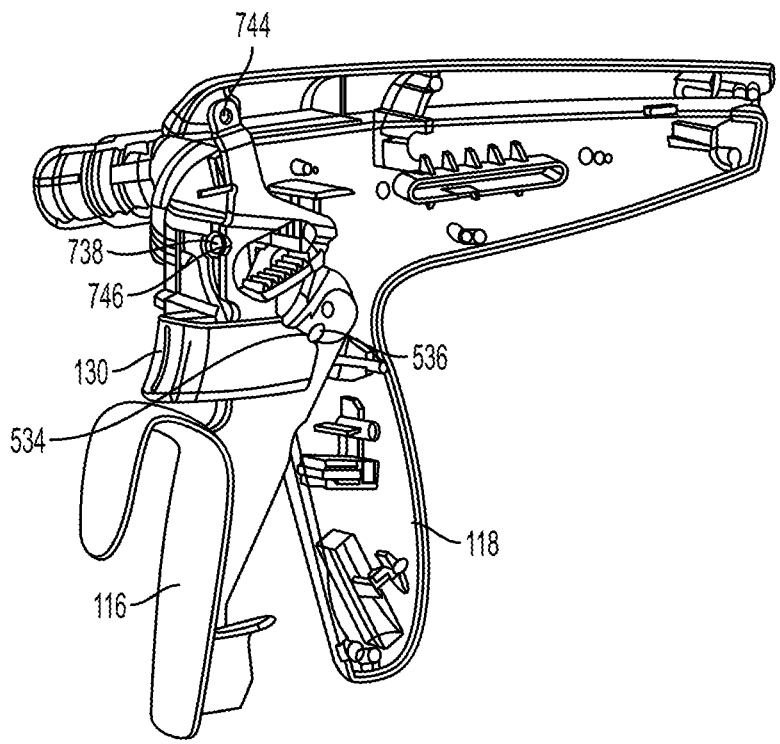
FIG. 7A is a front perspective view of a first actuator and a second actuator of the surgical instrument of FIG. 1, with some instrument components omitted for clarity of illustration.
Figure 7B:
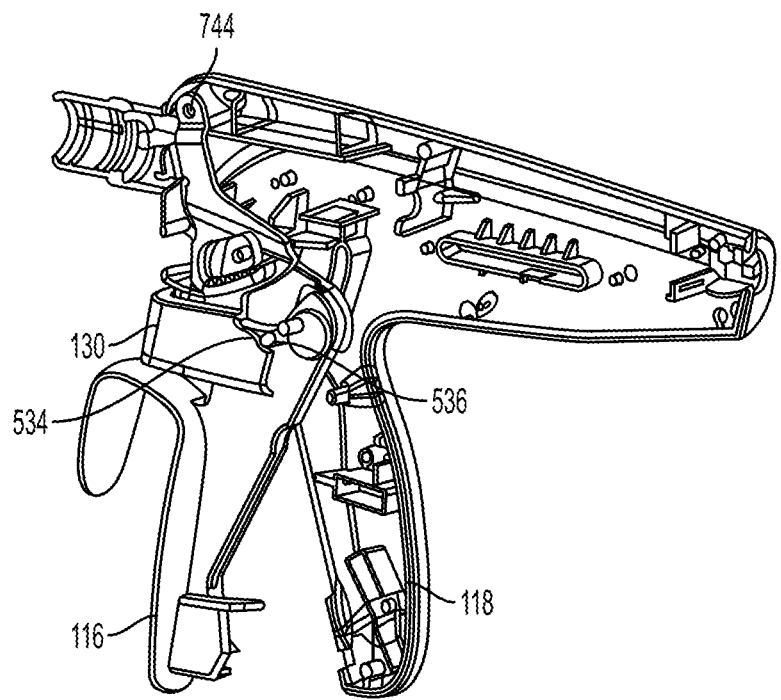
FIG. 7B is a rear perspective view of the first actuator and the second actuator of FIG. 7A.
Figure 8B:
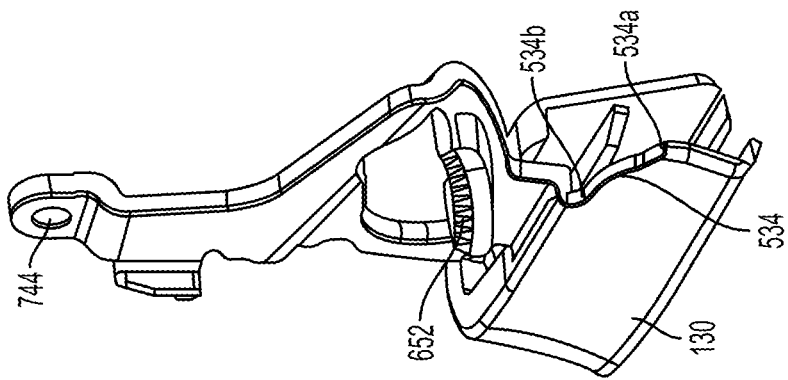
FIG. 8B is a rear perspective view of the first actuator of FIG. 8A.
Figure 8A:
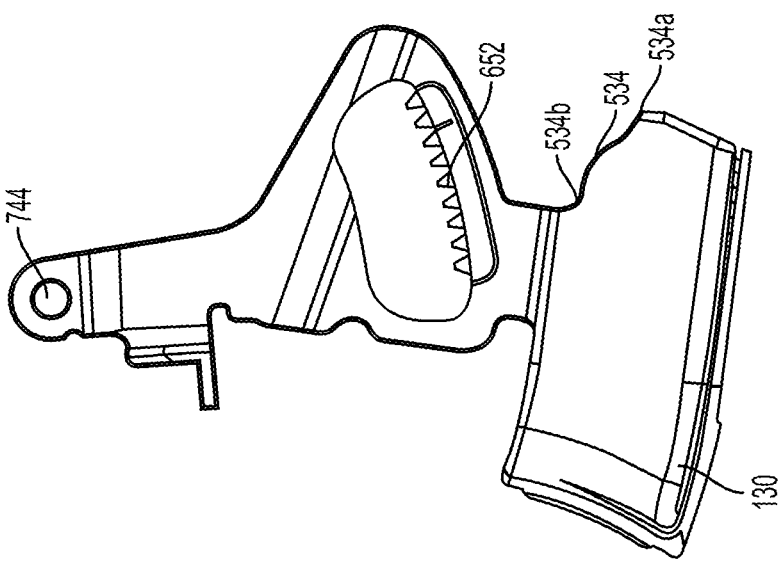
FIG. 8A is a front perspective view of the first actuator of the surgical instrument of FIG. 1.
Figure 10:
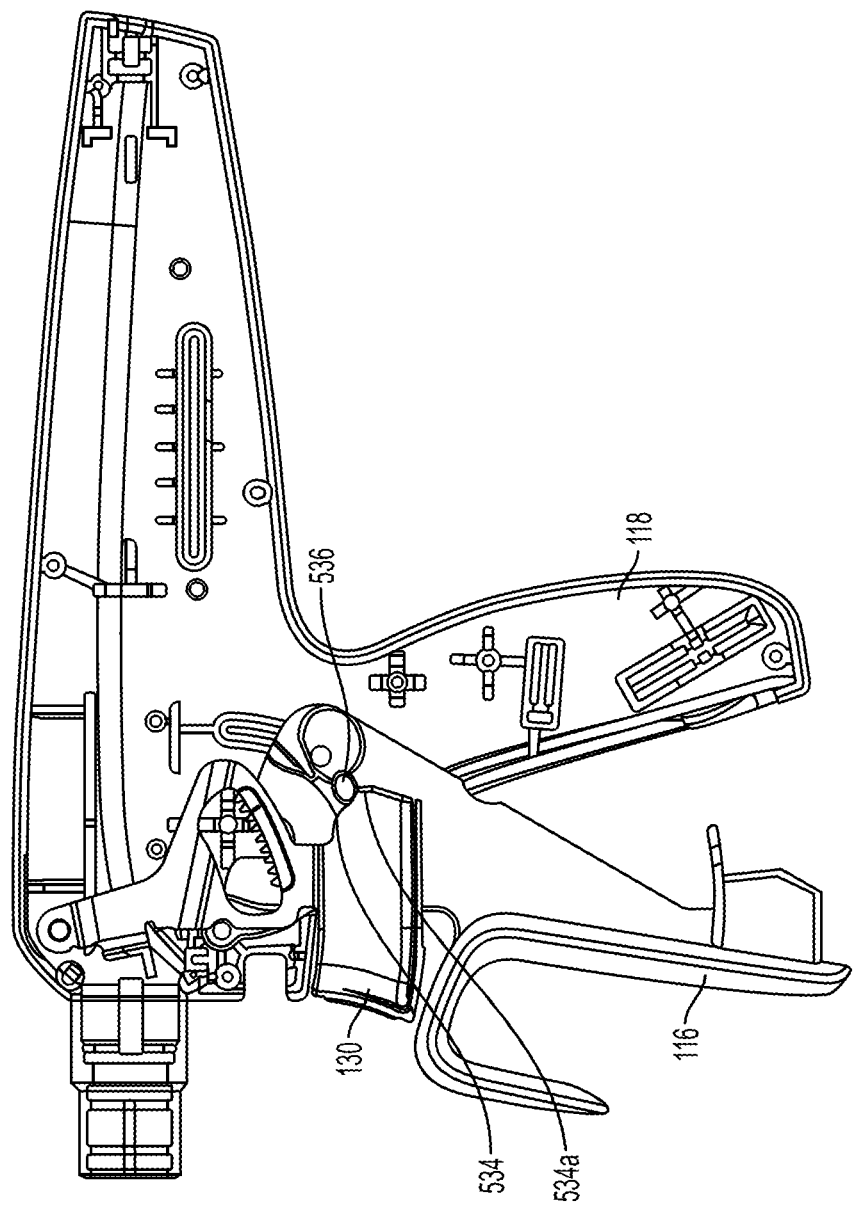
FIG. 10 is a side cutaway view of the first actuator and the second actuator of the surgical instrument of FIG. 1 in a first, released position with some instrument components omitted for clarity of illustration.
Figure 10A:
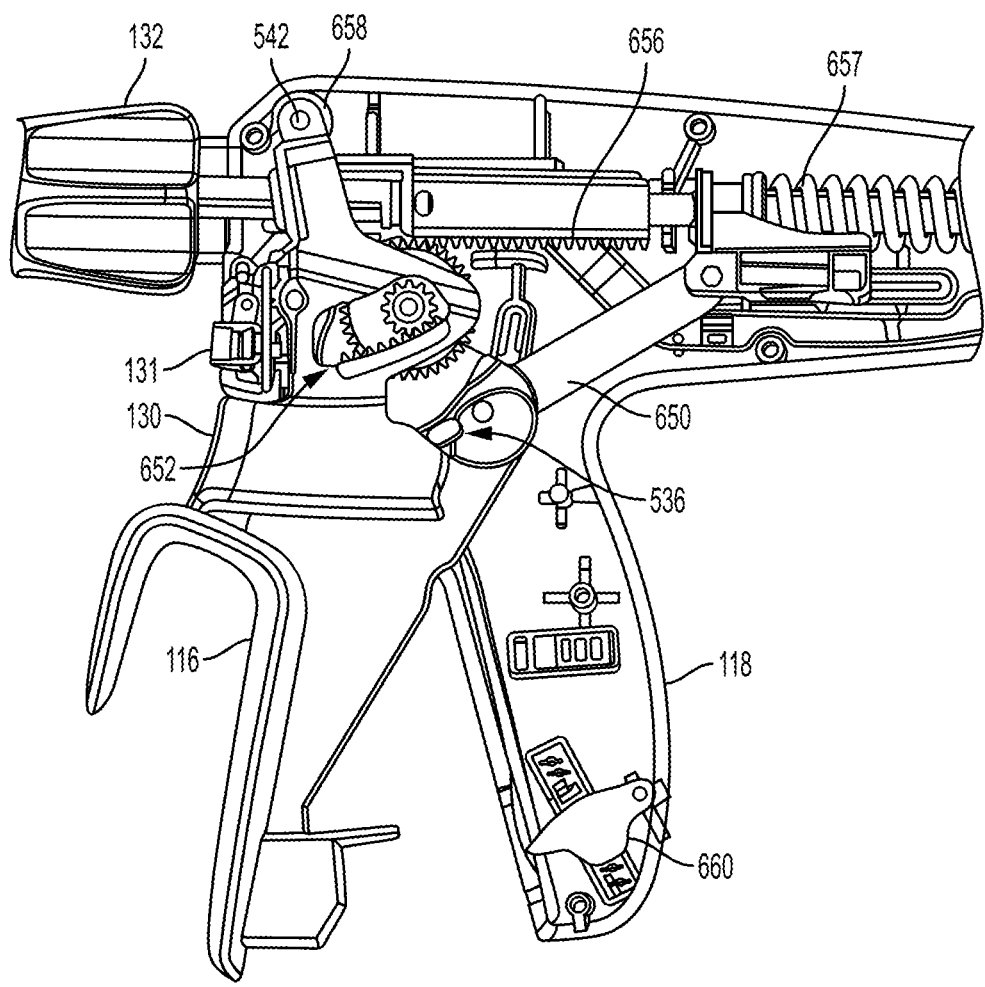
FIG. 10A is another side cutaway view of the first actuator and the second actuator of the surgical instrument of FIG. 1 in the first, released position.
Figure 11:
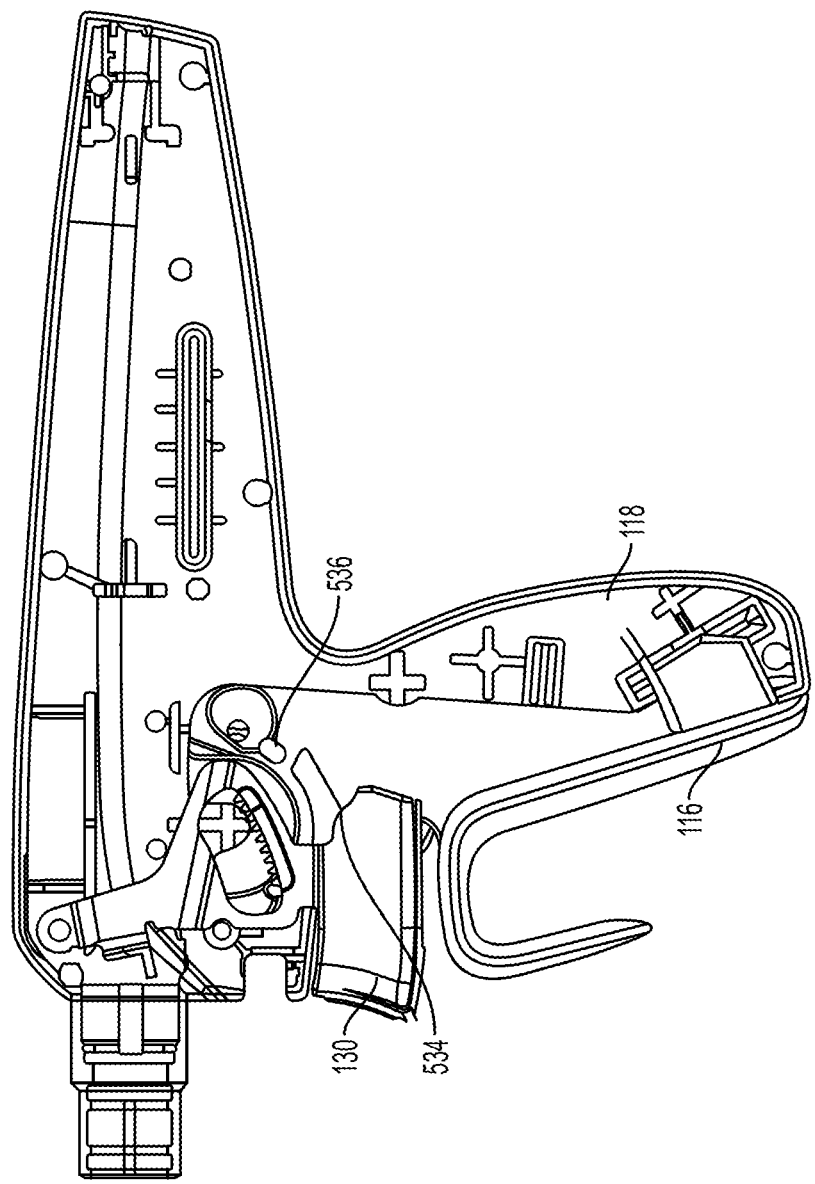
FIG. 11 is a side cutaway view of the first actuator and the second actuator of the surgical instrument of FIG. 1 wherein the first actuator is in a second, actuated position and the second actuator is in the first, released position, with some instrument components omitted for clarity of illustration.
Figure 11A:
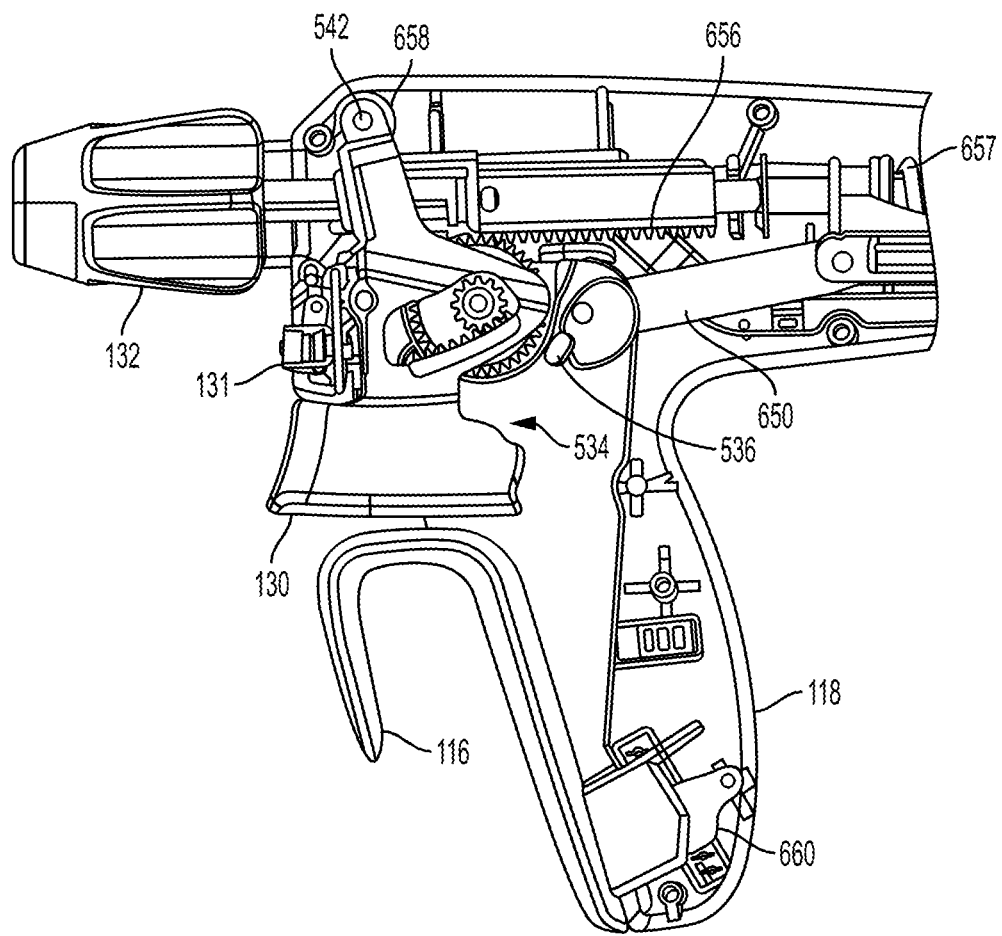
FIG. 11A is another side cutaway view of the first actuator and the second actuator of the surgical instrument of FIG. 1 with the first actuator in the second, actuated position and the second actuator in the first, released position.
Figure 12:
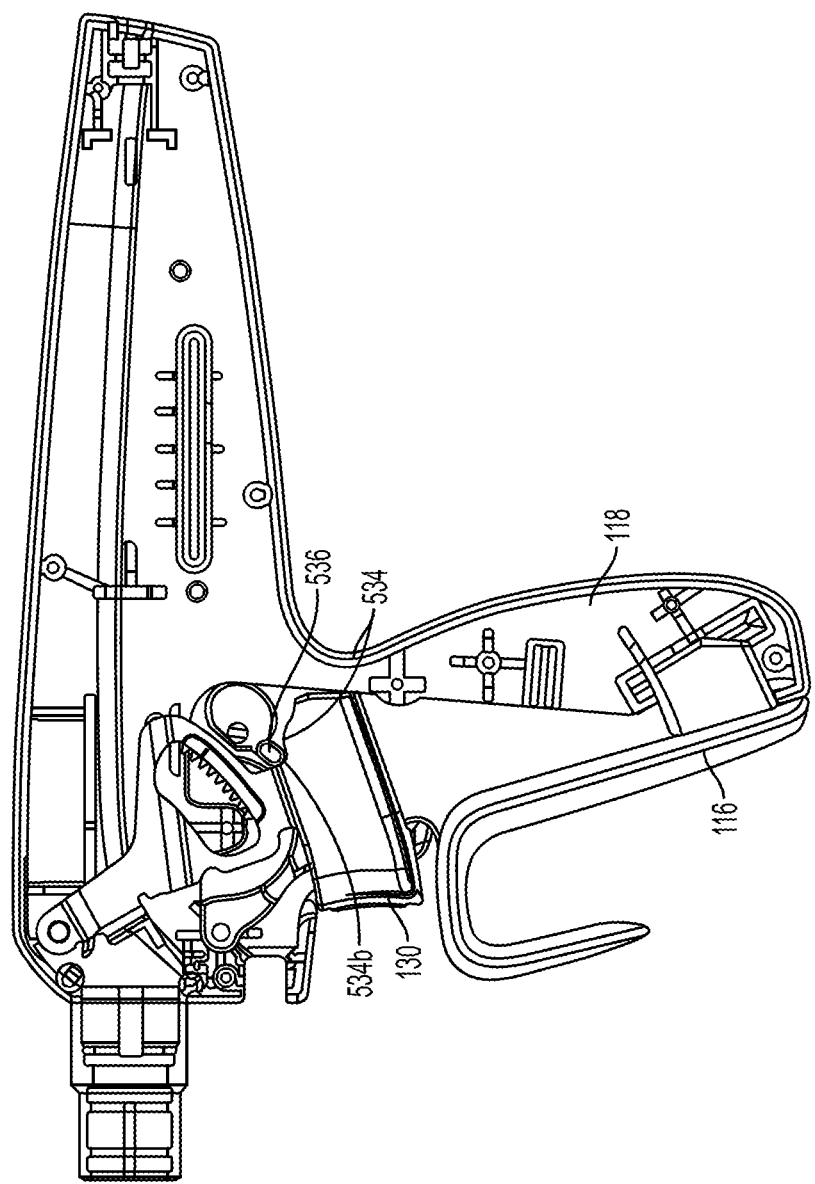
FIG. 12 is a side cutaway view of the first actuator and the second actuator of the surgical instrument of FIG. 1 in the second, actuated position, with some instrument components omitted for clarity of illustration.
Figure 12A:
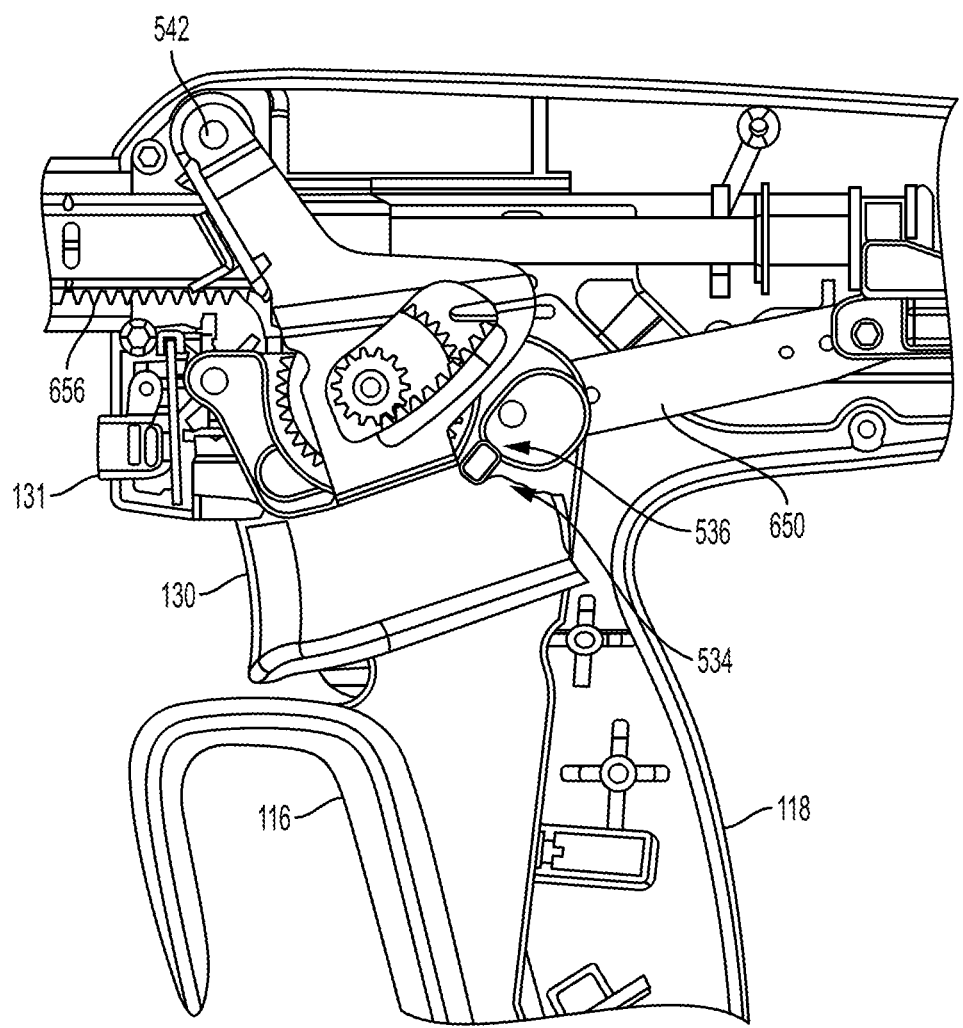
FIG. 12A is another side cutaway view of the first actuator and the second actuator of the surgical instrument of FIG. 1 with the first and second actuators in the second, actuated position.

FIGS. 5 and 6 show further details of the proximal actuator portion 110. For example, the first actuator 116 is shown pivotally coupled to the proximal actuator portion 110 by a pin 540. Such pivotal coupling of the first trigger 116 to the proximal actuator portion 110 allows the first actuator 116 to rotate pivotally between a first, released position, as shown in FIGS. 10 and 10A, and a second, actuated position, as shown in FIGS. 11 and 11A. Similarly, the second trigger 130 is shown pivotally coupled to the proximal actuator portion 110 by a pin 542. Such pivotal coupling of the second trigger 130 to the proximal actuator portion 110 can allow the second trigger 130 to rotate pivotally between a first, released position, as shown in FIGS. 11 and 11A, and a second, actuated position, as shown in FIGS. 12 and 12A.

The first actuator 116 can be configured to move the first and second jaws 120a, 120b of the end effector 114 between an open configuration and a closed configuration to clamp tissue therebetween, while the second actuator 130 can be configured to advance the cutting element 223 through tissue grasped between the first and second jaws 120a, 120b to transect the tissue. Movement of the first actuator 116 can be communicated to the end effector 114 using, e.g., the mechanical linkage 650, and movement of the second actuator 130 can be communicated to the cutting element 223 via, e.g., a pivoting rack 652 formed on the actuator 130, a rotating gear 654, and a translating rack 656. A variety of other configurations for transmitting movement of the first and second actuators 116, 130 to the end effector 114 are also possible and considered within the scope of the present disclosure.

In the illustrated embodiment, a first spring 657 and a second spring 658 can bias the first actuator 116 and the second actuator 130, respectively, to the first, released position shown in FIGS. 5 and 6. As a result, pressure is released on any of the first actuator 116 and the second actuator 130, (e.g., by releasing any pressure thereon urging the first actuator 116 or the second actuator 130 toward the stationary grip 118, as shown by the arrow P), the first and second actuators 116, 130 can return to the first, released position. Moreover, any biasing force imparted by the springs 657, 658 will have to be overcome when actuating any of the first actuator 116 and the second actuator 130. As mentioned above, the instrument 100 can include the latch or locking feature 660 configured to retain the first actuator 116 in the second, actuated position. A variety of other configurations for establishing a default or resting position for actuators are possible and are considered within the scope of the present disclosure.

Also shown in FIGS. 5 and 6 is the third actuator 131 that can be configured to control delivery of RF energy to tissue via one or more electrodes 221 disposed on the end effector jaws 120a, 120b. As noted above, in some embodiments the functionality of the third energy delivery actuator 131 can be incorporated into the second tissue transection actuator 130 such that the second actuator 130 activates energy delivery directly or indirectly (e.g., using a predetermined sequence of energy delivery and transection) via a direct electrical connection or a digital data processor or other controller. In addition, in some embodiments movement of the first and second actuators 116, 130 can be sensed using one or more sensors (not shown) and interpreted by one or more digital data processors acting as controllers 126. The one or more digital data processors can in some embodiments control activation of one or more motors 124 or other actuators to produce, e.g., distal end effector jaw movement, cutting element advancement, and/or tissue sealing energy delivery.

FIGS. 5 and 6 also illustrate a cam surface 534 and a cam follower 536 that can interact depending on the relative positions of the first and second actuators 116, 130 to ensure desired operation of the instrument 100. More particularly, the first actuator 116 can be coupled to or have formed thereon the cam follower 536, and the second actuator 930 can be coupled to or have formed thereon the cam surface 534. The cam surface 534 and the cam follower 536 can be configured to interact with one another based on the respective positions of the first actuator 116 and the second actuator 130. For example, when the first actuator 116 and the second actuator 130 are in the first, released or resting position (as shown in FIGS. 5, 6, 10, and 10A), the cam follower 536 can make contact with the cam surface 534. Conversely, when the first actuator 116 is in the second, actuated position and the second actuator 130 is in the first, released or resting position (as shown in FIGS. 11 and 11A) the cam surface 534 and the cam follower 536 can be separated from one another.

When the first and second actuators 116, 130 are in position relative to one another such that the cam follower 536 is in contact with the cam surface 534, movement of one actuator 116, 130 can cause proportional movement of the other actuator 116, 130 to prevent any undesirable or potentially unsafe end effector movement (e.g., extension of a cutting element when jaws are not sufficiently closed to prevent unintentional tissue damage). The proportional movement of one actuator 116, 130 in response to movement of the other actuator 116, 130 can be the result of interaction between the cam surface 534 and cam follower 536.

Figure 9B:
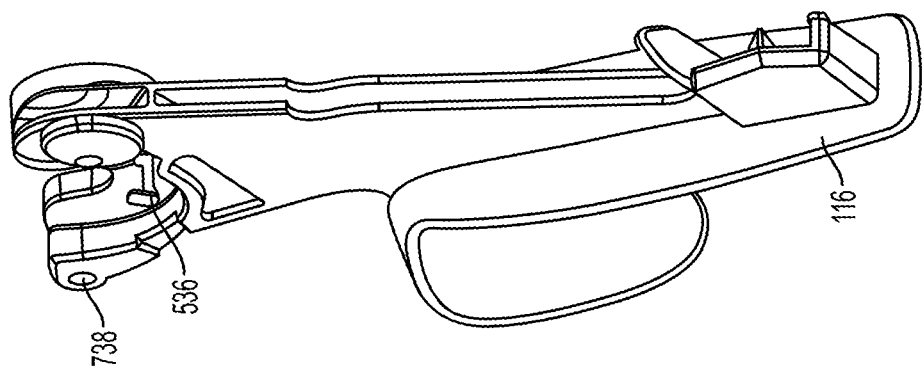
FIG. 9B is a rear perspective view of the second actuator of FIG. 9A.
Figure 9A:
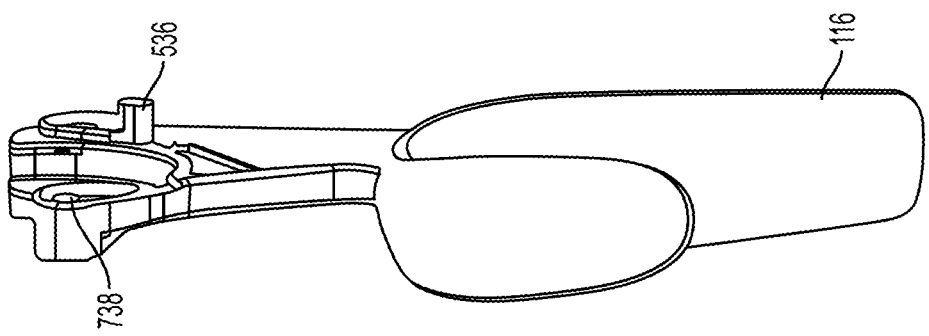
FIG. 9A is a side view of the second actuator of the surgical instrument of FIG. 1.

FIGS. 7A-9B illustrate the actuators 116, 130 in more detail. The cam surface 534 formed on the second actuator 130 can include a geometric shape configured to produce proportional movement of the first actuator 116 as the cam follower 536 moves along the cam surface 534 in response to actuation of the second actuator 130. The cam surface 534 can extend a length from a proximal end 534a to a distal end 534b, and can have a shape along its length (and especially at its ends) that prevents binding of the second actuator 130 to the first actuator 116. This can prevent the potentially undesirable scenario of, for example, the second actuator 130 becoming locked relative to the first actuator 116 when the first actuator 116 is in the second, actuated position. The cam follower 536, as best shown in FIGS. 9A and 9B, can have a generally round or elliptical shape and can be formed on an outer surface of the first actuator 116 at a position configured to interact with the cam surface 534.

The position-dependent interaction of the cam surface 534 and the cam follower 536 on the first and second actuators 116, 130 can result in cooperative movement of the actuators 116, 130 even when only a single actuator is depressed or otherwise manipulated. For example, actuation of the second actuator 130 when both the first actuator 116 and the second actuator 130 are in the first, released or resting position (as shown in FIGS. 7A, 7B, 10, and 10A) can cause a proportional and substantially simultaneous movement of the first actuator 116. By way of further explanation, when both the first and second actuators 116, 130 are in the first, released or resting position, the cam follower 536 can be in contact with (or positioned very close to without contacting) the cam surface 534 at the proximal end 534a of the cam surface. As pressure is applied to the second actuator 130 (e.g., by a user depressing the second actuator 130 toward the stationary grip 118, etc.), the second actuator 130 can rotate about the second pin 542 (denoted in FIGS. 7A-8B by the bore 744 through which the pin 542 is positioned) and the cam surface 534 can exert pressure on the cam follower 536. This pressure can, in turn, cause the first actuator 116 to rotate about the first pin 540 (denoted in FIGS. 7A, 7B, 9A, and 9B by the bore 738 through which the pin 540 is positioned). In such an instance, the movement of the first actuator 116 in relation to the movement of the second actuator 130 will be dependent on the geometric shape of the cam surface 534. Thus, the surgical instrument 100 can include a second actuator 130 having a cam surface 534 that is configured to move the first actuator 116 proportionally and substantially simultaneously in relation to the second actuator 130 such that the jaws 120a, 120b of the end effector 114 close sufficiently as the cutting element 223 is extended distally to avoid damage to the instrument 100 and unintentional damage to tissue. Given the different pivot points of the first and second actuators 116, 130, a relationship between movement of the two actuators 116, 130 may not be 1:1.

Moreover, the actuation force or pressure required to be applied to the second actuator 130 when both actuators 116, 130 start in the first, released position can be greater than the pressure required to operate the second actuator 130 when the first actuator 116 is already in the second, actuated position. This movement of both actuators 116, 130 simultaneously is required through cooperation of the cam surface 534 and cam follower 536 with less leverage than is available if the first actuator 116 is actuated directly. This increased impedance to actuation (i.e., required actuation force or pressure) can provide feedback to a user, e.g., suggesting that the instrument 100 is not being operated in an optimal manner. Despite providing feedback, however, such operation can be permitted if sufficient actuating force is applied to the second actuator 130. Accordingly, a user can be informed of non-standard or non-optimal operation, but such operation can be safely permitted because of the cooperative movement of the actuators 116, 130.

In another example, release of the first actuator 116 when both the first and second actuators 116, 130 are in the second, actuated position can result in proportional release of the second actuator 130 based on interaction between the cam surface 534 and the cam follower 536. When both the first actuator 116 and the second actuator 130 are in the second, actuated position (as shown in FIGS. 12 and 12A), the cam follower 536 can be in contact with (or positioned very close to without contacting) the cam surface 534 at a distal end 534b of the cam surface 534. As pressure is released from the first actuator 116 (e.g., by relaxing a user's grip, releasing the latch or locking feature 660, etc.), the first actuator 116 can rotate about the pin 540 and the spring 657 can urge the first actuator 116 away from the stationary grip 118 (i.e., toward the configuration shown in FIGS. 10 and 10A). The cam follower 536 can contact the cam surface 534 and slide along the cam surface 534 from the distal end 534b to the proximal end 534a thereof. This interaction can cause the cause the second actuator 130 to similarly move toward the first, released position proportionally with the first actuator 116. As a result, the cutting element 223 controlled by the second actuator 130 can be proportionally withdrawn proximally as the jaws 120a, 120b are opened to avoid damage to the instrument 100 or unintentional tissue damage.

While the above-described interactions focus on the first actuator 116 controlling jaw movement and the second actuator 130 controlling tissue transection, a variety of other end effector functions can be controlled by similar position-dependent cooperative elements coupled to or formed on various actuators. Such alternative embodiments are considered within the scope of the present disclosure.

As noted above, FIGS. 10-12A show various positions of the first actuator 116 and the second actuator 130 to illustrate the conditional cooperation between these components. More particularly, FIGS. 10 and 10A illustrate a configuration in which both the first actuator 116 and the second actuator 130 are in a first, released or resting position. FIGS. 11 and 11A illustrate a configuration in which the first actuator 116 is in a second, actuated position and the second actuator 130 remains in the first, released position. Finally, FIGS. 12 and 12A illustrate a configuration in which both the first actuator 116 and the second actuator 130 are in the second, actuated position.

The position-dependent cooperative features described herein, e.g., the cam surface 534 formed on the second actuator 130 and the cam follower 536 formed on the first actuator 116, can allow movement between the configurations of FIGS. 10-12A in a variety of manners. For example, a more standard mode of operation can be used, similar to that described above in connection with FIGS. 3 and 4, wherein the first actuator 116 is moved to the actuated position first (such as by moving from the configuration of FIGS. 10 and 10A to that of FIGS. 11 and 11A), followed by actuation of the second actuator 130 (such as by moving from the configuration of FIGS. 11 and 11A to that of FIGS. 12 and 12A). In such a method of actuation, the second actuator 130 can be moved from the released position to the actuated position independent of the first actuator 116, as it has already been moved such that the cam follower 536 is spaced apart from the cam surface 534.

Alternatively, the second actuator 130 can be actuated initially (such as by moving from the configuration of FIGS. 10 and 10A to that of FIGS. 12 and 12A). In such a method of actuation, interaction between the cam surface 534 on the second actuator 130 and the cam follower 536 on the first actuator 116 can cause the first actuator 116 to move toward an actuated position proportionally with the second actuator 130. Further, a user will experience a greater impedance to actuating the second actuator 130 due to the requirement of moving the first actuator 116 as well (and with less advantageous leverage than when the first actuator 116 is moved on its own).

Several different variations are possible when releasing the first and second actuators 116, 130. For example, the second actuator 130 can be released, followed by release of the first actuator 116 (such as by moving from the configuration of FIGS. 12 and 12A to that of FIGS. 11 and 11A and then that of FIGS. 10 and 10A). In such a method, the cam surface 534 and cam follower 536 can be separated and the actuators 116, 130 can be moved independently of one another. In another embodiment, however, the first actuator 116 can be released without first releasing the second actuator 130 (such as by moving from the configuration of FIGS. 12 and 12A to that of FIGS. 10 and 10A). In such an embodiment, the cam follower 536 can contact the cam surface 534 and cause the second actuator 130 to move proportionally with the first actuator 116 toward the first, released position.

Surgical methods are also described herein. In one embodiment, for example, a method can include moving a first actuator from a released position to an actuated position to bring first and second jaws of an end effector closer to one another. The method can further include moving a second actuator from a released position to an actuated position to translate a blade distally along a portion of the end effector. Further, moving the second actuator can cause proportional movement of the first actuator toward the actuated position if the first actuator is in the released position and can be independent of the first actuator if the first actuator is in the actuated position. In some embodiments, the method can further include moving the first actuator from the actuated position to the released position. Moreover, moving the first actuator from the actuated position to the released position can cause proportional movement of the second actuator toward the released position if the second actuator is in the actuated position and can be independent of the second actuator if the second actuator is in the released position. As noted above, several other steps are also possible, including, for example, delivering radio frequency (RF) energy to tissue grasped between the first and second jaws of the end effector, etc.

Another surgical method according to the present disclosure can include actuating the first actuator 116 of the surgical instrument 100. In some embodiments, actuating the second actuator 130 can cause a substantially simultaneous and proportional actuation of the first actuator 116, such that the first actuator 116 causes first and second jaws 120*a*, 120*b* of the surgical instrument 100 to move from an open configuration to a closed configuration to grasp tissue therebetween along with substantially simultaneous distal extension of the cutting element 223 to transect the grasped tissue clamped between the first and second jaws 120*a*, 120*b*.

In other embodiments, a surgical method can further include releasing the first actuator 116 when both the first actuator 116 and the second actuator 130 are in an actuated position (e.g., by pressure being applied to both the first and second actuators 116, 130). So long as pressure is maintained on the second actuator 130, the first actuator 116 can be held in an actuated positon by the interaction of the cam surface 534 and the cam follower 536. If the second actuator 130 is released, however, both the first actuator 116 and the second actuator 130 can substantially simultaneously and proportionally return to the first, released position. Other surgical methods, including alternative orders of operating various actuators, triggers, or other control mechanisms are possible and considered within the scope of the present disclosure.

The instruments disclosed herein can be formed from a variety of materials and can have a variety of different sizes and shapes. For example, instruments or components thereof can be formed from various polymers and/or metals. Furthermore, particular components can be formed from different materials than other components. By way of further example, a proximal actuator portion can be formed from a polymer material, (e.g., polycarbonate, etc.), while an end effector can be formed from a metal, such as surgical grade stainless steel (e.g., 17-4, etc.), other 300 and 400 series stainless steels, titanium, and aluminum, perhaps to take advantage of greater rigidity. Instrument sizes can also vary greatly, depending on the intended use and surgical site anatomy.

In some embodiments, the devices and methods described herein can be used in open surgical procedures, and in other embodiments, the devices and methods can be used in laparoscopic, endoscopic, and other minimally invasive surgical procedures. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

The instruments disclosed herein can be designed to be disposed of after a single use, or they can be designed to be used multiple times. In either case, however, the instrument can be reconditioned for reuse after at least one use. Reconditioning can include any combination of the steps of disassembly of the instrument, followed by cleaning or replacement of particular pieces, and subsequent reassembly. In particular, the instrument can be disassembled, and any number of the particular pieces or parts of the instrument can be selectively replaced or removed in any combination. Upon cleaning and/or replacement of particular parts, the instrument can be reassembled for subsequent use either at a reconditioning facility, or by a surgical team immediately prior to a surgical procedure. Those skilled in the art will appreciate that reconditioning of an instrument can utilize a variety of techniques for disassembly, cleaning/replacement, and reassembly. Use of such techniques, and the resulting reconditioned instrument, are all within the scope of the present disclosure.

The instruments described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the instrument due to the materials utilized, the presence of electrical components, etc.

One skilled in the art will appreciate further features and advantages of the disclosure based on the above-described embodiments. Accordingly, the disclosure is not to be limited by what has been particularly shown and described, except as indicated by the appended claims. All publications and references cited herein are expressly incorporated herein by reference in their entirety.

What is claimed is:

1. A surgical method, comprising:
   moving a first actuator of a surgical instrument from a released position to an actuated position and thereby bring first and second jaws of an end effector of the surgical instrument closer to one another; and
   moving a second actuator of the surgical instrument from a released position to an actuated position and thereby translate a cutting element along a portion of the end effector relative to the first and second jaws and thereby cut tissue between the jaws with the cutting element and cause proportional movement of the first actuator toward the actuated position when the first actuator is in the released position, the movement of the second actuator from the released position to the actuated position being independent of the first actuator when the first actuator is in the actuated position.

2. The surgical method of claim 1, further comprising moving the first actuator from the actuated position to the released position;

wherein moving the first actuator from the actuated position to the released position causes proportional movement of the second actuator toward the released position when the second actuator is in the actuated position, and the movement of the first actuator from the actuated position to the released position is independent of the second actuator when the second actuator is in the released position.

3. The surgical method of claim 1, wherein the end effector is at a distal end of the surgical instrument, and the translation of the cutting element is distal translation along the portion of the end effector relative to the first and second jaws.

4. The surgical method of claim 1, wherein the first actuator includes a cam follower and the second actuator includes a cam surface, the cam follower and the cam surface being configured to move into and out of contact one another depending on relative positions of the first actuator and the second actuator.

5. The surgical method of claim 4, wherein the cam follower and the cam surface are configured to prevent binding of the second actuator to the first actuator when the first actuator and the second actuator are in the actuated position.

6. The surgical method of claim 4, wherein the cam follower and the cam surface are configured to be spaced apart from one another when the first actuator is in the actuated position.

7. The surgical method of claim 4, wherein the cam follower and the cam surface are configured to contact one another such that movement of the first actuator from the actuated position to the released position is effective to move the second actuator proportionally toward the released position unless the second actuator is already in the released position.

8. The surgical method of claim 1, wherein a force required to move the second actuator to the actuated position when the first actuator and the second actuator are in the released position is greater than a force required to move the second actuator to the actuated position when the first actuator is in the actuated position and the second actuator is in the released position.

9. The surgical method of claim 1, wherein the second actuator is configured to move from the released position to the actuated position regardless of a position of the first actuator.

10. The surgical method of claim 1, wherein each of the first actuator and the second actuator includes a trigger pivotally coupled to a housing.

* * * * *